(12) United States Patent
Tokur (10) Patent No.: US 10,828,405 B2
(45) Date of Patent: Nov. 10, 2020

(54) PLEURAL DRAINAGE SET AND PLEURAL DRAINAGE METHOD

(71) Applicant: Mahmut Tokur, Kahramanmaraş (TR)

(72) Inventor: Mahmut Tokur, Kahramanmaraş (TR)

( * ) Notice: Subject to any disclaimer, the term of this patent is extended or adjusted under 35 U.S.C. 154(b) by 684 days.

(21) Appl. No.: 15/531,727

(22) PCT Filed: Nov. 28, 2014

(86) PCT No.: PCT/TR2014/000479
§ 371 (c)(1),
(2) Date: May 30, 2017

(87) PCT Pub. No.: WO2016/085421
PCT Pub. Date: Jun. 2, 2016

(65) Prior Publication Data
US 2017/0312408 A1    Nov. 2, 2017

(51) Int. Cl.
*A61M 1/00* (2006.01)
*A61M 1/04* (2006.01)
(Continued)

(52) U.S. Cl.
CPC ........... *A61M 1/04* (2013.01); *A61B 17/3211* (2013.01); *A61M 1/0013* (2013.01); *A61M 1/0023* (2013.01); *A61M 1/0064* (2013.01); *A61M 1/0086* (2014.02); *A61M 25/09* (2013.01); *A61M 27/00* (2013.01); *A61M 39/24* (2013.01); *A61B 2017/320052* (2013.01); *A61M 2202/048* (2013.01); *A61M 2205/0205* (2013.01); *A61M 2210/101* (2013.01)

(58) Field of Classification Search
CPC ... A61B 17/3211; A61B 2017/320052; A61M 1/0013; A61M 1/0023; A61M 1/0064; A61M 1/0086; A61M 1/04; A61M 2202/048; A61M 2205/0205; A61M 2210/101; A61M 25/09; A61M 27/00; A61M 39/24
See application file for complete search history.

(56) References Cited

U.S. PATENT DOCUMENTS

| 4,888,000 A | * | 12/1989 | McQuilkin | ....... A61M 25/0668 604/164.05 |
| 5,300,106 A | * | 4/1994 | Dahl | ....... A61N 1/05 604/164.05 |

(Continued)

FOREIGN PATENT DOCUMENTS

| CN | 201 135 499 Y | 10/2008 |
| CN | 201135499 Y | 10/2008 |

(Continued)

OTHER PUBLICATIONS

International Search Report, dated Oct. 30, 2015 for corresponding International Application No. PCT/TR2014/000479.
(Continued)

*Primary Examiner* — Kai H Weng
(74) *Attorney, Agent, or Firm* — Bradley D. Crose; Crose Law LLC (57) ABSTRACT

A single use pleural drainage set for medical use, which allows drainage by all physicians of air (pneumothorax), blood (hemothorax) and all other liquids (hydrothorax) accumulated abnormally in the thoracic cavity (pleural space (I)).

5 Claims, 4 Drawing Sheets (51) Int. Cl.
*A61B 17/3211* (2006.01)
*A61M 25/09* (2006.01)
*A61M 27/00* (2006.01)
*A61M 39/24* (2006.01)
*A61B 17/32* (2006.01)

(56) References Cited

U.S. PATENT DOCUMENTS

| | | | | |
|---|---|---|---|---|
| 6,261,276 | B1* | 7/2001 | Reitsma | A61M 1/0023 |
| | | | | 604/319 |
| 7,695,467 | B2 | 4/2010 | Breznock et al. | |
| 2014/0324000 | A1* | 10/2014 | Hill | A61M 27/00 |
| | | | | 604/328 |

FOREIGN PATENT DOCUMENTS

| | | |
|---|---|---|
| CN | 202314571 U | 7/2012 |
| CN | 202 478 249 U | 10/2012 |
| CN | 202478249 U | 10/2012 |
| CN | 203 043 070 U | 7/2013 |
| CN | 203043070 U | 7/2013 |
| WO | WO 2013/064922 A1 | 5/2013 |

OTHER PUBLICATIONS

Written Opinion of the ISA, dated Oct. 30, 2015 for corresponding International Application No. PCT/TR2014/000479.

* cited by examiner

PLEURAL DRAINAGE SET AND PLEURAL DRAINAGE METHOD

CROSS-REFERENCE TO RELATED APPLICATIONS

This application is a U.S. National Phase application, under 35 U.S.C. § 371, of International Application no. PCT/TR2014/000479 with an international filing date of Nov. 28, 2014, and which is hereby incorporated by reference for all purposes.

TECHNICAL FIELD

The invention is for medical usage purpose and related to single use pleural drainage set, which allows drainage by all physicians of air (pneumothorax), blood (hemothorax) and all other liquids (hydrothorax) accumulated abnormally in the thoracic cavity (pleural space).

STATE OF THE ART

Today, closed underwater drainage is applied generally with tube thoracostomy method in treatment of pleural space diseases including pneumothorax, hemothorax and hydrothorax.

Tube thoracostomy is the method of placing pipe shaped drains at different shapes and diameters and manufactured with various raw materials in the pleural space through the ribs in a surgical operation. This operation is generally made at hospital environment and by specialist physicians. Furthermore, sterilized surgical tools are required to be used during this operation.

Challenges of the Current Technique are

The patient should be brought to the hospital environment for tube thoracostomy. On the other hand, some emergency cases may result in death if this method is not applied at the scene of incident.

Tube thoracostomy should be applied by authorized specialist physicians. Otherwise, fatal complications may develop during tube thoracostomy rendered by unprofessional medical personnel.

Sometimes it can result in death of the patient if there is not enough time for the authorized specialist physician to intervene in the patient.

Tube thoracostomy requires many medical materials and surgical tools. These materials may not be available in sterilized condition at an easily accessible distance at all times.

In some emergency cases, it is required to intervene in the patient at current location. There may not be the possibility or enough time to take the patient to the hospital or the surgical intervention or operation room at the hospital. It can result in death of the patient on such occasions.

Chest injuries caused by traffic accidents, fall, gunfire and sharp objects or stab wounds are extremely fatal. Even when the ambulance or medical teams arrive at the scene on time, the patient can lose his/her life at the scene or in the ambulance as there is not any surgical material available at the scene and any authorized specialist physician for rendering intervention.

There are certain solution offers to problems about available drainage methods in the current technique. Examples are provided below.

One example to solution offers for aforementioned problems is the U.S. Patent application/certificate titled "Method and apparatus for chest drainage" numbered "U.S. Pat. No. 7,695,467 B2".

Another example is the Chinese utility model application/certificate titled "Disposable pleural effusion and pneumatosis drainage device" numbered "CN202314571 (U)".

In conclusion, due to insufficiency in the concerned field of the available solutions described in the aforementioned documents, there occurs the necessity for a single use pleural drainage set which allows drainage by all physicians of air (pneumothorax), blood (hemothorax) and all other liquids (hydrothorax) accumulated abnormally in the pleural space.

BRIEF DESCRIPTION OF THE INVENTION

The current invention is about an innovation, which fulfills the aforementioned requirements, eliminates all disadvantages and brings certain additional advantages in pleural drainage tools.

The main purpose of the invention is to be used in treatment of diseases including pneumothorax, hemothorax and hydrothorax.

One purpose of the invention is to be available as a sterilized set ready for use at all times at the scene of incident, in ambulances and at all hospital units. While tube thoracostomy can be applied at hospitals and generally at operation conditions in the current technique, the invention can be applied at all conditions and environments thanks to easy use and easy access provided by the invention. On the other hand, drainage can be applied without the need for diagnosis techniques (x-ray, tomography etc.) as there is a very low risk of lung injury during intervention. Therefore, application can be rendered to patients at the scene of incident in a safe and fast manner.

One purpose of the invention is to be applied by all physicians and emergency response teams in an easy, rapid and safe manner without the need for any surgical tools. While tube thoracostomy takes long due to aforementioned disadvantages in the current technique, it can be completed in a shorter time with the new method.

One purpose of the invention is to be used by all physicians and emergency response teams. While tube thoracostomy can only be applied by field specialist physicians in the current technique, the invention can be applied by all physicians and emergency medical technicians.

One purpose of the invention is to be single use and to remain sterilized at all times. In closed underwater drainage method with tube thoracostomy in the current technique, certain sterilized surgical tools are required to place the chest tube in the patient. In our invention, the set is single use and available in sterile condition.

While the chest drain and the drainage bottle are provided separately in the current technique, they are available in a combined single set in the invention. In the current technique, drainage bottles have large volumes and the volume is not adjustable by compressing or other methods and this increases storage and transportation cost of the bottle. In our invention, volume can be reduced by compressing the corrugated structure of the drainage bottle and it turns back to its former shape when released. Therefore, storage and transportation cost is reduced, the need for storage area is reduced and it becomes easy to maintain it at all conditions. This is one of the important purposes of the invention.

One purpose of the invention is to remove the need for stitches to prevent detachment of the tube after it is attached to the patient.

The structural properties and characteristics and all advantages of the invention can be clearly understood with below drawings and detailed descriptions of the drawings and assessment should be made considering these drawings and their detailed descriptions.

DRAWINGS OF THE INVENTION

"PLEURAL DRAINAGE METHOD WITH PLEURAL DRAINAGE SET" in our application is described in the attached drawings and these drawings are as follows.

Drawings should not be necessarily scaled and unnecessary details for understanding the invention may be omitted. Other elements that are at least mainly equivalent to each other or that have at least mainly equivalent functions to each other are indicated with the same number.

DESCRIPTION OF PART REFERENCES

Pleural Drainage Apparatus (1) and Components

1. Pleural drainage apparatus
2. Drain
3. Hole
4. Balloon
5. Balloon channel
6. Cover
7. Lock apparatus
8. Check valve apparatus
9. Guide wire channel
10. Guide wire
11. Washing channel
12. Closing apparatus
13. Connection apparatus
14. Protection layer

Pipe Type Cutting Guide (15) and Components

15. Pipe type cutting guide
16. Propelling apparatus
17. Stopper apparatus

Drainage Bottle (18) and Components

18. Drainage bottle
19. Air discharge channel
20. Air discharge channel cover
21. Lifting handle
22. Balance apparatus

Connection Pipe (23) and Components

23. Connection pipe
24. Underwater pipe
25. Outer pipe
26. Combination apparatus

Other Components

27. Injector
28. Scalpel
29. Antiseptic impregnated pad
30. Local anesthesia medication
I. Pleural space
II. Lung
III. Chest wall
IV. Intercostal space
V. Rib
VI. Washing liquid (all types of liquid)

DESCRIPTION OF PROCESS STEPS

101. Apply disinfection and anesthesia in the rib cage on the side to be intervened in the patient to be treated, 102. If necessary, incision on the skin with the scalpel (28), 103. Following application of disinfection and anesthesia in the body part to be intervened, hold the propelling apparatus (16) of the pipe type cutting guide (15) and place the cutting end in the pleural space between the ribs (V) with the help of propelling force, 104. Advance the drain (2) with the perforated end (3) first through the pipe type cutting guide (15) and place it in the pleural space (I), 105. Remove the pipe type cutting guide (15) from the skin and the pleural drainage apparatus (1), 106. Place the drain (2) at a desired location in the pleural space (I) with the guide wire (10).

DETAILED DESCRIPTION OF THE INVENTION

In this detailed description, the preferred embodiments of "PLEURAL DRAINAGE METHOD WITH PLEURAL DRAINAGE SET" of the present invention are only described for better understanding the invention without causing any limiting affect.

Figure 1:
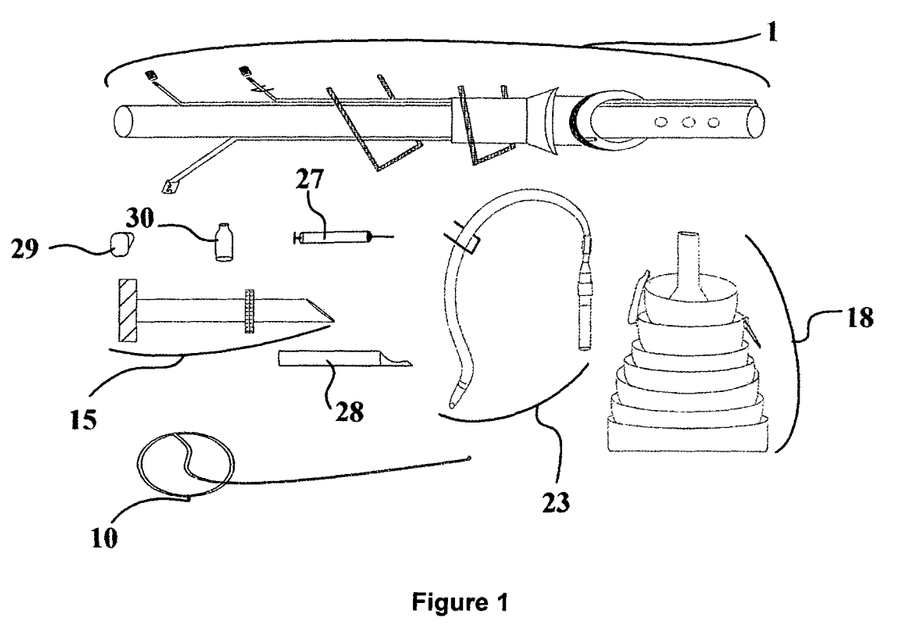
FIG. 1: Representative view of the pleural drainage set of the present invention.
Figure 2:
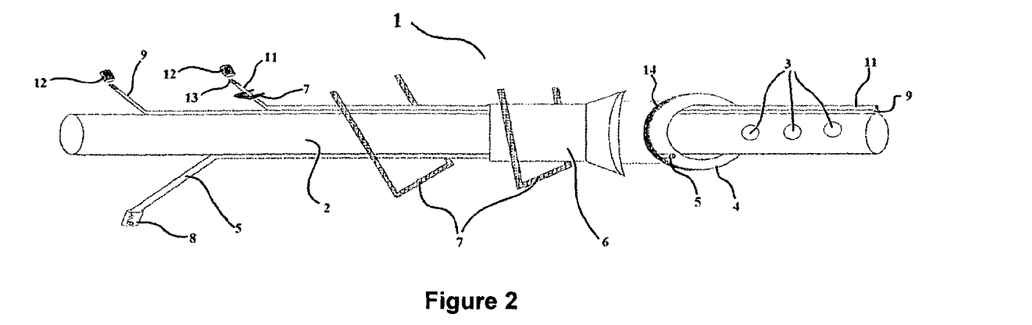
FIG. 2: Representative view of the pleural drainage apparatus (1) in the pleural drainage set of the present invention.

Furthermore, some components in the detailed description can be used in various forms for better understanding and content integrity in the sentence. Components in various statements represent the component with the same number. The pleural drainage set in the invention comprises of:
  Pleural drainage apparatus (1),
  Pipe type cutting guide (15) in a disintegrable structure by dividing into two on the long axis, which is located on the outer part of the drain (2), is larger than the drain (2) diameter and allows placing the drain (2) in the pleural space (I) through two ribs,
  Drainage bottle (18) which has a corrugated or accordion shape and can be reduced or enlarged by size,
  Connection pipe (23) which provides connection between the drain (2) and the drainage bottle (18),
  Injector (27),
  Scalpel (28),
  Antiseptic impregnated pad (29),
  Local anesthesia medication (30).
Pleural drainage apparatus (1) comprises of:
  Drain (2) made of any kind of plastic and equivalent raw material,
  At least one hole (3) on the drain (2), Balloon (4) which can be located at various points on the drain (2) and can be inflated and deflated, Balloon channel (5) used to inflate or deflate the balloon (4), To ensure that the drain is maintained in the human body without the need for stitches, an empty and moving cover (6) on the drain (2) which can be in various appearances, lock apparatus (7) which has a locking mechanism to ensure immobility by fixing the cover (6) on the drain (2) between the balloon (4) and itself, Cover (6) and lock apparatus (7) can be manufactured integrated or separate Lock apparatus (7) which is used to prevent air and liquid flow by compressing and blocking the drain (2) and to close the open end of the guide wire channel (9), Check valve apparatus (8) designed to prevent backflow of liquid or air fed in this channel with the help of an injector for inflating the balloon apparatus (4) on the back end of the balloon channel (5), Guide wire channel (9) closed in one end which directs the drain (2) to desired area after its first entrance in the pleural space between the ribs (V), Guide wire (10) which is located in the guide wire channel (9) and directs the drain (2) to desired area after its first entrance in the pleural space, Washing channel (11) open in two ends which allows washing the pleural space (I) with liquids including serum (VI) after the drain (2) is placed in the pleural space, Closing apparatus (12) which is used to close one open end of the washing channel (11), Connection apparatus (13) which allows connection of the washing channel (11) with other external catheters, Protection layer (14) which covers the outer surface of the drain (2), the balloon channel (5), the guide wire channel (9) and the washing channel (11) and prevents the lock apparatus (7) from blocking these parts.

Figure 4:
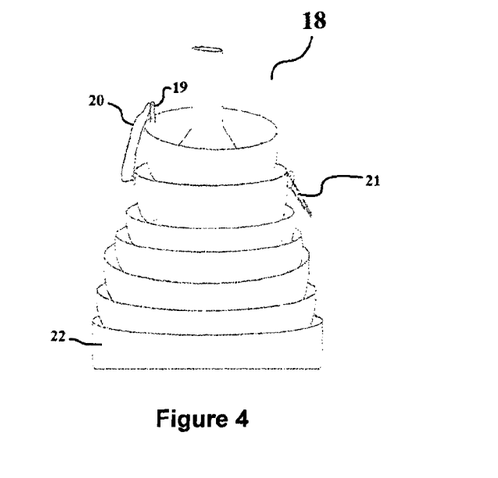
FIG. 4: Representative view of the drainage bottle (18) in the pleural drainage set of the present invention.
Figure 5:
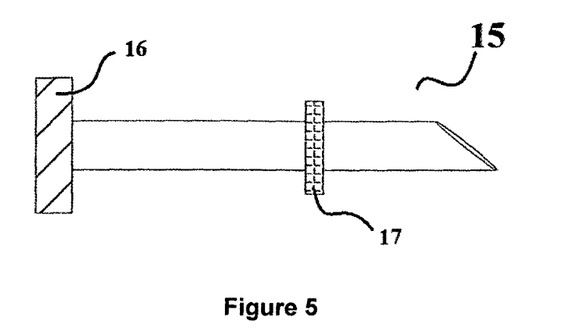
FIG. 5: Representative view of the pipe type cutting guide (15) in the pleural drainage set of the present invention.

Pipe type cutting guide (15) comprises of:

Propelling apparatus (16) designed disintegrable by dividing into two, which is located in the rear end of the pipe type cutting guide (15) and which allows placing the pipe type cutting guide (15) manually in the pleural space (I), Stopper apparatus (17) designed disintegrable by dividing into two, which is located in the cutting front end of the pipe type cutting guide (15) and which prevents placing the pipe type cutting guide (15) in the pleural space more than a determined distance, Drainage bottle (18) comprises of:

Air discharge channel (19) on the drainage bottle (18),

Air discharge channel cover (20) on the drainage bottle (18),

Lifting handle (21) of the drainage bottle (18),

Balance apparatus (22), which ensures balanced standing of the drainage bottle (18).

Figure 3:
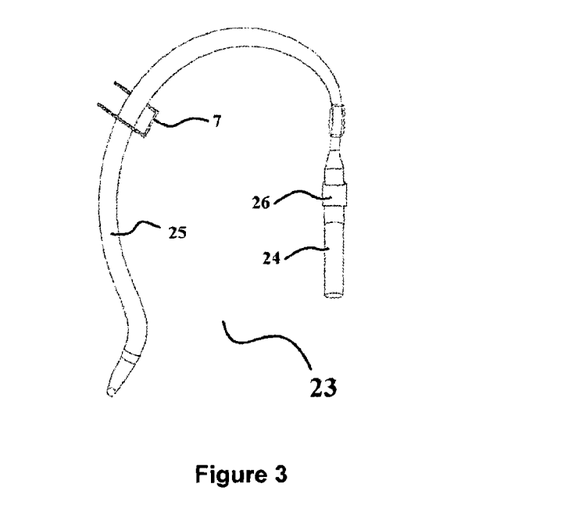
FIG. 3: Representative view of the connection pipe (23) in the pleural drainage set of the present invention.

Connection pipe (23) comprises of:

Underwater pipe (24) on the end of the connection pipe (23),

Outer pipe (25) which prevents twisting of the connection pipe (23),

Combination apparatus (26) which allows combination of the connection pipe (23) and the drainage bottle (18).

Cover (6); This cover (6) is located at the back of the balloon apparatus (4) and is larger than the drain (2) diameter, thus it can move on the drain (2). It is open on both ends and can have an appearance in the form of funnel, circle, ellipsis or other shapes.

Parts of the pleural drainage apparatus (1) other than the guide wire (10) and the pipe type cutting guide (15) can be manufactured with PVC, silicon or equivalent raw materials. The guide wire (10) and the pipe type cutting guide (15) are manufactured with metal and derivatives and inner and outer parts of them can be covered partially or completely with plastic or equivalents.

In the pleural drainage apparatus (1), the drain (2) and the balloon inflation channel (5) and the guide wire channel (9) and the washing channel (11) are located one on top of another and attached to each other. All these parts are monolithic.

The drain (2) is open in both ends and there is at least one or more hole(s) (3) at various sizes and diameters on the front end. The drain (2) can be manufactured at different sizes and diameters.

The balloon channel (5) has one open end, the open end is terminated in the balloon (4), the other end is closed with the check valve apparatus (8). The balloon (4) can be manufactured at different diameters depending on the measurements of the drain (2).

The end of the washing channel (11) which enters in the pleural space (I) is open and the other end which does not enter in the pleural space (I) can be covered with various apparatuses.

The end of the guide wire channel (9) which enters in the pleural space (I) is closed and the other end which does not enter in the pleural space (I) can be covered with various apparatuses.

There is a Protection layer (14) which covers the outer surface of the drain (2), the balloon channel (5), the washing channel (11) and the guide wire channel (9) and which begins from the back of the balloon (4) and extends to the part of the drain (2) which does not enter in the pleural space (I). The protection layer (14) is monolithic with the drain.

The pipe type cutting guide (15) is an apparatus with open ends which is sharp in the front end and has a grip (16) for easy manual handling. There is a stopper apparatus (17) which is located close to the sharp front end and which lets certain amount of entrance of the pipe type cutting guide (15) in the pleural space (I).

USE OF INVENTION

Figure 6:
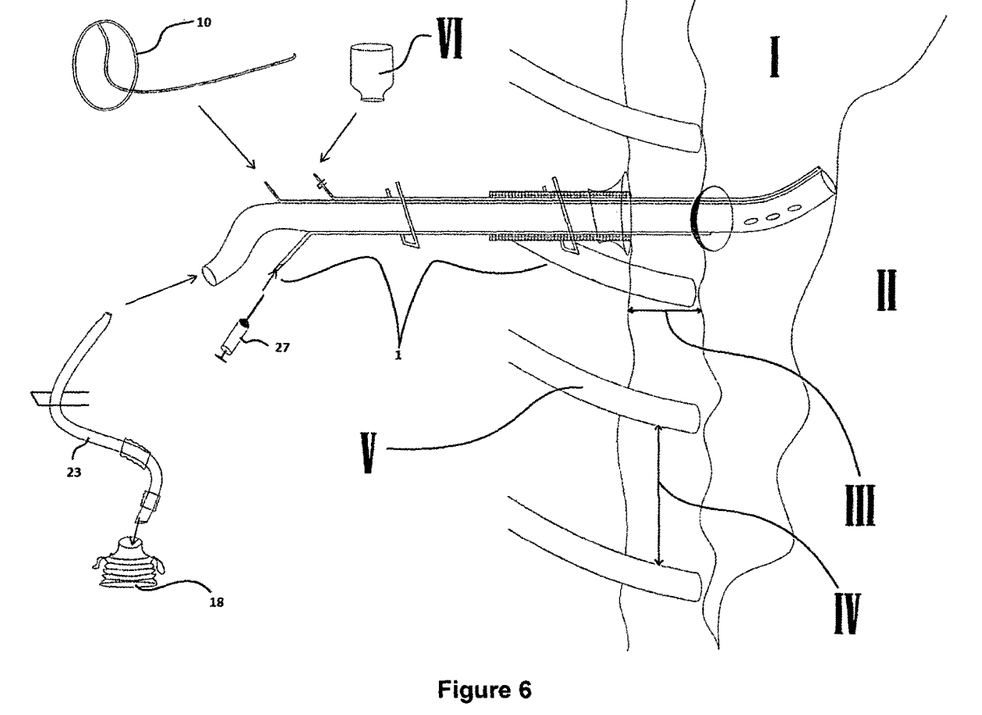
FIG. 6: Representative view of the application of the pleural drainage set of the present invention to the body.
Figure 7:
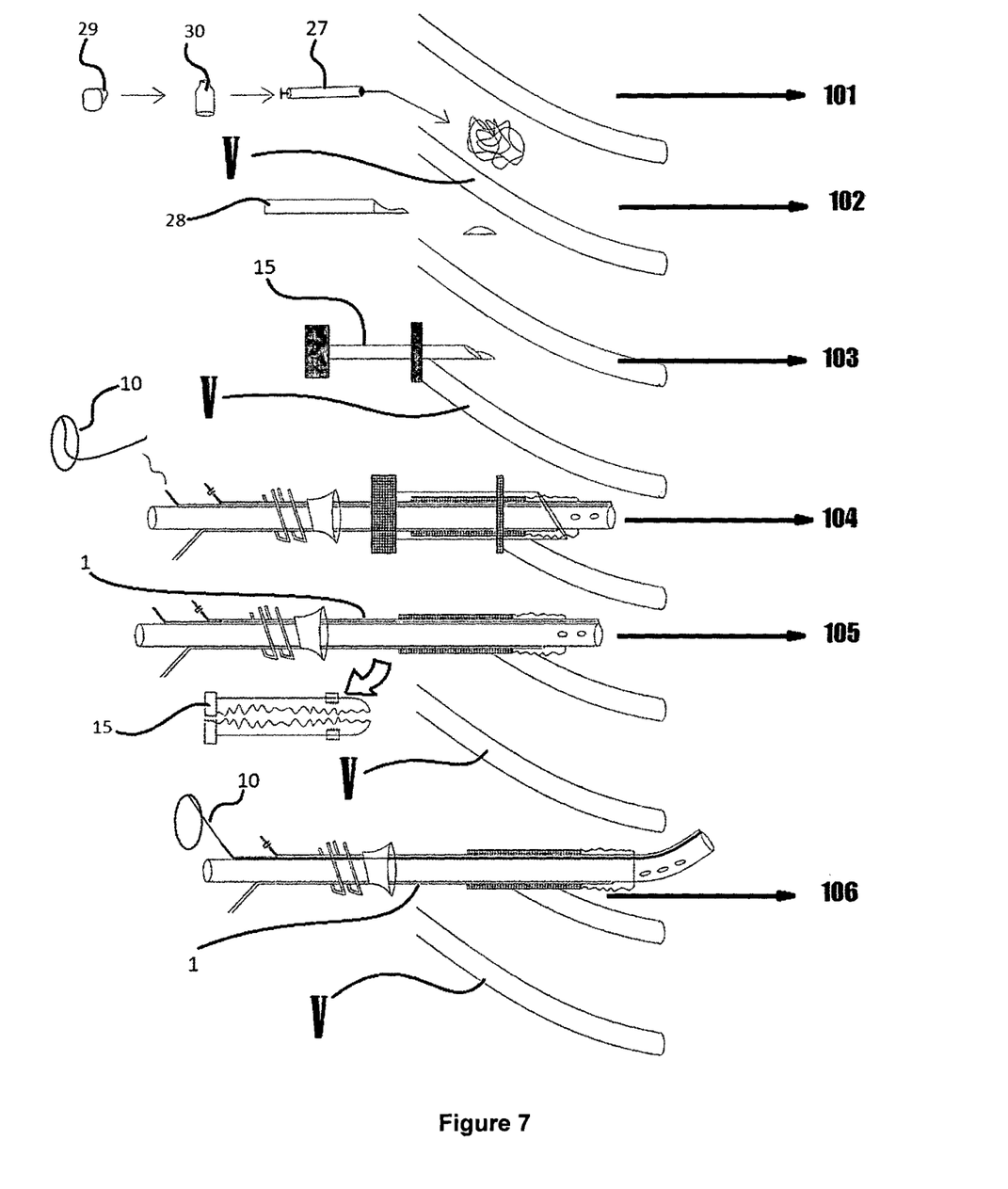
FIG. 7: Representative view of the placement of the pleural drainage set of the present invention in the pleural space.

Disinfection and anesthesia are applied in the rib cage on the side to be intervened in the patient to be treated. Following application of disinfection and anesthesia in the body part to be intervened, the propelling apparatus (16) of the pipe type cutting guide (15) is held and the sharp end is placed in the pleural space (I) passing by the chest wall (III) through the ribs (V) (the intercostal space) (IV) with the help of propelling force. If necessary, the skin can be cut with the scalpel (28). The drain (2), first in the perforated end (3) is placed in the pleural space (I) by advancing through the pipe type cutting guide (15). The drain (2) can be located at a desired location in the pleural space (I) with the guide wire (10). Then it is connected to the drainage bottle (18) with the connection pipe (23).

After the drain (2) is located in the pleural space (I), the balloon (4) is inflated in the pleural space (I), thus the drain (2) is prevented from coming out of the pleural space (I). When the balloon (4) is deflated, it does not prevent the drain (2) from coming out.

The balloon inflation channel (5) ensures air or liquid necessary for inflation of the balloon (4) reach inside the balloon (4). The balloon inflation channel (5) and the drain (2) are located one on top of another and they are integrated.

The balloon inflation channel (5) is a pipe with open ends; the front end is terminated in the balloon (4). The rear end is open and is terminated in the check valve (8). The check valve (8) is an apparatus, which allows one direction air or liquid flow. With the help of an injector (27) at the back, air or liquid is transferred to the balloon (4) through the balloon inflation channel (5). Thus, the balloon (4) is inflated.

After the balloon (4) is inflated in the pleural space (I), the cover (6) on the drain (2) is screwed on outer side of the ribs (V) with the locking apparatus (7) and displacement of the drain (2) is prevented. Thus, the drain is attached to the chest wall (III) without stitching.

The drain (2) is connected to the drainage bottle (18) through the connection pipe (23), thus air, blood or liquid in the pleural space (I) is transferred to the drainage bottle (18).

With the air discharge channel (19) on the drainage bottle (18), when the patient coughs, pneumothorax air is discharged from the pleural space (I) to the atmosphere. The air discharge channel cover (20) is designed to ensure that the drainage bottle (18) makes drainage from the pleural space (I) with vacuum effect.

The lock apparatus (7) on the connection pipe (23) allows closing down the connection pipe when necessary. Therefore, it is used when the drain (2) needs to be closed down for interventions including intrapleural lavage by feeding washing liquid (VI) from the washing channel (11) into the pleural space (I) or pleurodesis or for other reasons.

The pipe type cutting guide (15) ensures that the drain (2) can be located in the pleural space (I) without the need for a surgical tool. This pipe type cutting guide (15) which is similar to the cutting apparatus in the pleurogeneous catheter has a propelling apparatus (16) on the rear end as distinct from the apparatus in the pleurogeneous catheter and thus, the drain (2) can be located only manually between the two ribs (V). The stopper apparatus (17) on the pipe type cutting guide (15) prevents excess entrance in the pleural space (I) and possible lung (II) injuries. As distinct from the apparatus in the pleurogeneous catheter, the rear end of the pipe type cutting guide (15) is not closed but open, it slightly makes pneuomothorax at the first entrance in the pleural space (I) and reduces the risk of lung (II) injury.

There is not need for suturing thanks to the balloon (4), the cover (6) and the lock apparatus (7) developed to eliminate suture, which is required to prevent the drain (2) from coming out of the patient.

While interventions including washing the pleural space (I) and pleurodesis are completed by feeding liquid through the drain in the current technique, they are made through the washing channel (11), which is integrated with the drain (2) in the invention.

Based on this main concept, it is possible to develop various applications in this pleural drainage set in the invention designed for pleural space drainage, the invention cannot be limited with examples herein and it is mainly as described in the claims section.

The invention claimed is:

1. A single use pleural drainage set which allows drainage by all physicians of air (pneumothorax), blood (hemothorax) and all other liquids (hydrothorax) accumulated abnormally in the thoracic cavity (pleural space (I)), characterized in that the pleural drainage set comprises:
   a pleural drainage apparatus (1);
   a pipe type cutting guide (15) in a disintegrable structure by dividing into two on a longitudinal axis, which is located on an outer part of the drain (2), is larger than a diameter of a drain (2) and allows placing the drain (2) in the pleural space (I) between two ribs (V);
   a drainage bottle (18) which has a corrugated or accordion shape and is configured to reduce and enlarge;
   a connection pipe (23) which provides connection between the drain (2) and the drainage bottle (18);
   an injector (27);
   a scalpel (28);
   an antiseptic impregnated pad (29);
   a local anesthesia medication (30).

2. The pleural drainage set according to claim 1, wherein the drainage bottle (18) comprises:
   an air discharge channel (19) on the drainage bottle (18);
   an air discharge channel cover (20) on the drainage bottle (18);
   a lifting handle (21) on the drainage bottle (18);
   a balance apparatus (22), which ensures balanced standing of the drainage bottle (18).

3. The pleural drainage set according to claim 1, wherein the connection pipe (23) comprises:
   an underwater pipe (24) on an end of the connection pipe (23);
   an outer pipe (25) which prevents twisting of the connection pipe (23);
   a combination apparatus (23), which allows combination of the connection pipe (23) and the drainage bottle (18).

4. The pleural drainage set according to claim 1, wherein the pleural drainage apparatus (1) comprises:
   the drain (2) made of a plastic and equivalent raw material;
   at least one hole (3) on the drain (2);
   a balloon (4) configured to be located at various points on the drain (2) and is capable of being inflated and deflated;
   a balloon channel (5) used to inflate or deflate the balloon (4);
   an empty and moving cover (6) on the drain (2) configured to have various shapes including a funnel, a round, or an ellipse appearance, and is larger than a diameter of the drain (2) and located behind the balloon (4) on the drain (2);
   a lock apparatus (7) which has a locking mechanism to ensure immobility by fixing the cover (6) on the drain (2) between the balloon (4) and the lock apparatus;
   wherein the cover (6) and the lock apparatus (7) are manufactured integrated or separate, the lock apparatus (7) is used to prevent air and liquid flow by compressing and blocking the drain (2) and to close an open end of a guide wire channel (9),
   a check valve apparatus (8) designed to prevent backflow of liquid or air fed in the balloon channel with the help of an injector for inflating the balloon (4) on a back end of the balloon channel (5);
   the guide wire channel (9) closed in one end which directs the drain (2) to a desired area after the guide wire channel first enters in the pleural space through the ribs (V);
   a guide wire (10) which is located in the guide wire channel (9) and directs the drain (2) to the desired area after the guide wire first enters in the pleural space;
   a washing channel (11) open in two ends which allows washing the pleural space (I) with liquids including serum after the drain (2) is placed in the pleural space;
   a closing apparatus (12) which is used to close one open end of the washing channel (11);
   a connection apparatus (13) which allows connection of the washing channel (11) with other external catheters;
   a protection layer (14) which covers an outer surface of the drain (2), the balloon channel (5), the guide wire channel (9) and the washing channel (11) and prevents the lock apparatus (7) from blocking these parts.

5. The pleural drainage set according to claim 1, wherein the pipe type cutting guide (15) comprises:
   a propelling apparatus (16) designed disintegrable by dividing into two, which is located in a rear end of the pipe type cutting guide (15) and which allows placing the pipe type cutting guide (15) manually in the pleural space (I);
   a stopper apparatus (17) designed disintegrable by dividing into two, which is located in a cutting front end of the pipe type cutting guide (15) and which prevents placing the pipe type cutting guide (15) in the pleural space (I) more than a determined distance.

* * * * *